United States Patent
Horn et al.

(10) Patent No.: US 10,321,946 B2
(45) Date of Patent: Jun. 18, 2019

(54) RENAL NERVE MODULATION DEVICES WITH WEEPING RF ABLATION BALLOONS

(71) Applicant: Boston Scientific Scimed, Inc., Maple Grove, MN (US)

(72) Inventors: Daniel J. Horn, Shoreview, MN (US); Cass A. Hanson, St. Paul, MN (US); Derek C. Sutermeister, Ham Lake, MN (US); Timothy A. Ostroot, Cokato, MN (US); Daniel T. Quillin, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 789 days.

(21) Appl. No.: 13/975,021

(22) Filed: Aug. 23, 2013

(65) Prior Publication Data
US 2014/0058376 A1 Feb. 27, 2014

Related U.S. Application Data

(60) Provisional application No. 61/693,066, filed on Aug. 24, 2012.

(51) Int. Cl.
*A61B 18/14* (2006.01)
*A61B 18/04* (2006.01)
(Continued)

(52) U.S. Cl.
CPC .......... *A61B 18/04* (2013.01); *A61B 18/1492* (2013.01); *A61B 18/18* (2013.01);
(Continued)

(58) Field of Classification Search
CPC .. A61B 2018/0022; A61B 2018/00238; A61B 18/1492; A61B 2018/00255
See application file for complete search history.

(56) References Cited

U.S. PATENT DOCUMENTS

| 164,184 A | 6/1875 | Kidder |
|---|---|---|
| 1,167,014 A | 1/1916 | O'Brien |
(Continued)

FOREIGN PATENT DOCUMENTS

| DE | 10038737 A1 | 2/2002 |
|---|---|---|
| EP | 1053720 A1 | 11/2000 |
(Continued)

OTHER PUBLICATIONS

US 8,398,630 B2, 03/2013, Demarais et al. (withdrawn)
(Continued)

*Primary Examiner* — Jaymi E Della

(57) ABSTRACT

The disclosure pertains to an intravascular catheter, comprising an elongate member having a proximal end and a distal end, a balloon having an interior surface, an exterior surface, a lumen defined by the interior surface and a cylindrical wall extending between the interior surface and the exterior surface, the cylindrical wall having a proximal end and a distal end, the balloon having a plurality of weeping windows disposed in the wall and able to pass an electric current between the interior surface and the exterior surface and wherein the balloon wall is otherwise electrically insulative, and an electrode disposed in the balloon. The intravascular system is suited for modulation of renal nerves, for example.

20 Claims, 10 Drawing Sheets

(51) Int. Cl.
  *A61B 18/18* (2006.01)
  *A61N 5/00* (2006.01)
  *A61M 25/10* (2013.01)
  *A61B 18/00* (2006.01)

(52) U.S. Cl.
  CPC ...... *A61N 5/00* (2013.01); *A61B 2018/00285* (2013.01); *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/00821* (2013.01); *A61B 2018/1472* (2013.01); *A61M 2025/1086* (2013.01)

(56) References Cited

U.S. PATENT DOCUMENTS

| | | |
|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,547,472 A * | 8/1996 | Onishi ............... A61M 25/104 604/103.01 |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |

(56) References Cited

U.S. PATENT DOCUMENTS

| | | |
|---|---|---|
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A * | 8/1998 | Swanson ............ A61L 29/085 600/374 |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A * | 11/1998 | Panescu ............ A61B 18/1492 600/374 |
| 5,830,222 A | 11/1998 | Makower |
| 5,832,228 A | 11/1998 | Holden et al. |
| 5,833,593 A | 11/1998 | Liprie |
| 5,836,874 A * | 11/1998 | Swanson ............ A61B 18/1492 600/374 |
| 5,840,076 A * | 11/1998 | Swanson ............ A61L 29/085 606/34 |
| 5,843,016 A | 12/1998 | Lugnani et al. |
| 5,846,238 A * | 12/1998 | Jackson ............ A61B 18/1492 600/374 |
| 5,846,239 A * | 12/1998 | Swanson ............ A61N 1/05 606/41 |
| 5,846,245 A | 12/1998 | McCarthy et al. |
| 5,848,969 A | 12/1998 | Panescu et al. |
| 5,853,411 A * | 12/1998 | Whayne ............ A61B 18/1492 600/374 |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A * | 2/1999 | Swanson ............ A61B 18/1492 606/34 |
| 5,871,483 A * | 2/1999 | Jackson ............ A61B 18/1492 600/374 |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A * | 3/1999 | Owens ............ A61B 18/1492 600/374 |
| 5,891,114 A | 4/1999 | Chien et al. |
| 5,891,135 A * | 4/1999 | Jackson ............ A61B 18/1492 600/374 |
| 5,891,136 A * | 4/1999 | McGee ............ A61B 18/1492 600/374 |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A * | 7/1999 | Panescu ............ A61B 18/1492 600/374 |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A * | 10/1999 | Swanson ............ A61B 18/1492 606/34 |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |

(56) References Cited

U.S. PATENT DOCUMENTS

| | | | |
|---|---|---|---|
| 6,024,740 | A | 2/2000 | Lesh |
| 6,030,611 | A | 2/2000 | Gorecki et al. |
| 6,032,675 | A | 3/2000 | Rubinsky et al. |
| 6,033,397 | A | 3/2000 | Laufer et al. |
| 6,033,398 | A | 3/2000 | Farley et al. |
| 6,036,687 | A | 3/2000 | Laufer et al. |
| 6,036,689 | A | 3/2000 | Tu et al. |
| 6,041,260 | A | 3/2000 | Stern et al. |
| 6,050,994 | A | 4/2000 | Sherman et al. |
| 6,056,744 | A | 5/2000 | Edwards |
| 6,056,746 | A | 5/2000 | Goble et al. |
| 6,063,085 | A | 5/2000 | Tay et al. |
| 6,066,096 | A | 5/2000 | Smith et al. |
| 6,066,139 | A | 5/2000 | Ryan et al. |
| 6,068,638 | A | 5/2000 | Makower |
| 6,068,653 | A | 5/2000 | Lafontaine |
| 6,071,277 | A | 6/2000 | Farley et al. |
| 6,071,278 | A * | 6/2000 | Panescu ............ A61B 18/1492 606/34 |
| 6,078,839 | A | 6/2000 | Carson |
| 6,079,414 | A | 6/2000 | Roth |
| 6,080,171 | A | 6/2000 | Keith et al. |
| 6,081,749 | A | 6/2000 | Ingle et al. |
| 6,086,581 | A | 7/2000 | Reynolds et al. |
| 6,093,166 | A | 7/2000 | Knudson et al. |
| 6,096,021 | A | 8/2000 | Helm et al. |
| 6,099,526 | A * | 8/2000 | Whayne ............ A61B 18/1492 600/374 |
| 6,102,908 | A | 8/2000 | Tu et al. |
| 6,106,477 | A | 8/2000 | Miesel et al. |
| 6,110,187 | A | 8/2000 | Donlon et al. |
| 6,114,311 | A | 9/2000 | Parmacek et al. |
| 6,117,101 | A | 9/2000 | Diederich et al. |
| 6,117,128 | A | 9/2000 | Gregory |
| 6,120,476 | A | 9/2000 | Fung et al. |
| 6,120,516 | A | 9/2000 | Selmon et al. |
| 6,121,775 | A | 9/2000 | Pearlman |
| 6,123,679 | A | 9/2000 | Lafaut et al. |
| 6,123,682 | A | 9/2000 | Knudson et al. |
| 6,123,702 | A | 9/2000 | Swanson et al. |
| 6,123,703 | A | 9/2000 | Tu et al. |
| 6,123,718 | A | 9/2000 | Tu et al. |
| 6,129,725 | A | 10/2000 | Tu et al. |
| 6,135,997 | A | 10/2000 | Laufer et al. |
| 6,142,991 | A | 11/2000 | Schatzberger et al. |
| 6,142,993 | A | 11/2000 | Whayne et al. |
| 6,149,647 | A | 11/2000 | Tu et al. |
| 6,152,899 | A | 11/2000 | Farley et al. |
| 6,152,912 | A | 11/2000 | Jansen et al. |
| 6,156,046 | A | 12/2000 | Passafaro et al. |
| 6,158,250 | A | 12/2000 | Tibbals et al. |
| 6,159,187 | A | 12/2000 | Park et al. |
| 6,159,225 | A | 12/2000 | Makower |
| 6,161,048 | A | 12/2000 | Sluijter et al. |
| 6,162,184 | A | 12/2000 | Swanson et al. |
| 6,165,163 | A | 12/2000 | Chien et al. |
| 6,165,172 | A | 12/2000 | Farley et al. |
| 6,165,187 | A | 12/2000 | Reger et al. |
| 6,168,594 | B1 | 1/2001 | Lafontaine et al. |
| 6,171,321 | B1 | 1/2001 | Gifford, III et al. |
| 6,179,832 | B1 | 1/2001 | Jones et al. |
| 6,179,835 | B1 | 1/2001 | Panescu et al. |
| 6,179,859 | B1 | 1/2001 | Bates et al. |
| 6,183,468 | B1 | 2/2001 | Swanson et al. |
| 6,183,486 | B1 | 2/2001 | Snow et al. |
| 6,190,379 | B1 | 2/2001 | Heuser et al. |
| 6,191,862 | B1 | 2/2001 | Swanson et al. |
| 6,197,021 | B1 | 3/2001 | Panescu et al. |
| 6,200,266 | B1 | 3/2001 | Shokrollahi et al. |
| 6,203,537 | B1 | 3/2001 | Adrian |
| 6,203,561 | B1 | 3/2001 | Ramee et al. |
| 6,210,406 | B1 | 4/2001 | Webster |
| 6,211,247 | B1 | 4/2001 | Goodman |
| 6,217,576 | B1 | 4/2001 | Tu et al. |
| 6,219,577 | B1 | 4/2001 | Brown, III et al. |
| 6,228,076 | B1 | 5/2001 | Winston et al. |
| 6,228,109 | B1 | 5/2001 | Tu et al. |
| 6,231,516 | B1 | 5/2001 | Keilman et al. |
| 6,231,587 | B1 | 5/2001 | Makower |
| 6,235,044 | B1 | 5/2001 | Root et al. |
| 6,236,883 | B1 | 5/2001 | Ciaccio et al. |
| 6,237,605 | B1 | 5/2001 | Vaska et al. |
| 6,238,389 | B1 | 5/2001 | Paddock et al. |
| 6,238,392 | B1 | 5/2001 | Long |
| 6,241,666 | B1 | 6/2001 | Pomeranz et al. |
| 6,241,753 | B1 | 6/2001 | Knowlton |
| 6,245,020 | B1 | 6/2001 | Moore et al. |
| 6,245,045 | B1 | 6/2001 | Stratienko |
| 6,248,126 | B1 | 6/2001 | Lesser et al. |
| 6,251,128 | B1 | 6/2001 | Knopp et al. |
| 6,258,087 | B1 | 7/2001 | Edwards et al. |
| 6,273,886 | B1 | 8/2001 | Edwards et al. |
| 6,280,466 | B1 | 8/2001 | Kugler et al. |
| 6,283,935 | B1 | 9/2001 | Laufer et al. |
| 6,283,959 | B1 | 9/2001 | Lalonde et al. |
| 6,284,743 | B1 | 9/2001 | Parmacek et al. |
| 6,287,323 | B1 | 9/2001 | Hammerslag |
| 6,290,696 | B1 | 9/2001 | Lafontaine |
| 6,292,695 | B1 | 9/2001 | Webster, Jr. et al. |
| 6,293,942 | B1 | 9/2001 | Goble et al. |
| 6,293,943 | B1 | 9/2001 | Panescu et al. |
| 6,296,619 | B1 | 10/2001 | Brisken et al. |
| 6,298,256 | B1 | 10/2001 | Meyer |
| 6,299,379 | B1 | 10/2001 | Lewis |
| 6,299,623 | B1 | 10/2001 | Wulfman |
| 6,309,379 | B1 | 10/2001 | Willard et al. |
| 6,309,399 | B1 | 10/2001 | Barbut et al. |
| 6,311,090 | B1 | 10/2001 | Knowlton |
| 6,317,615 | B1 | 11/2001 | KenKnight et al. |
| 6,319,242 | B1 | 11/2001 | Patterson et al. |
| 6,319,251 | B1 | 11/2001 | Tu et al. |
| 6,322,559 | B1 | 11/2001 | Daulton et al. |
| 6,325,797 | B1 | 12/2001 | Stewart et al. |
| 6,325,799 | B1 | 12/2001 | Goble |
| 6,328,699 | B1 | 12/2001 | Eigler et al. |
| 6,346,074 | B1 | 2/2002 | Roth |
| 6,346,104 | B2 | 2/2002 | Daly et al. |
| 6,350,248 | B1 | 2/2002 | Knudson et al. |
| 6,350,276 | B1 | 2/2002 | Knowlton |
| 6,353,751 | B1 | 3/2002 | Swanson et al. |
| 6,355,029 | B1 | 3/2002 | Joye et al. |
| 6,357,447 | B1 | 3/2002 | Swanson et al. |
| 6,361,519 | B1 | 3/2002 | Knudson et al. |
| 6,364,840 | B1 | 4/2002 | Crowley |
| 6,371,965 | B2 | 4/2002 | Gifford, III et al. |
| 6,375,668 | B1 | 4/2002 | Gifford et al. |
| 6,377,854 | B1 | 4/2002 | Knowlton |
| 6,377,855 | B1 | 4/2002 | Knowlton |
| 6,379,352 | B1 | 4/2002 | Reynolds et al. |
| 6,379,373 | B1 | 4/2002 | Sawhney et al. |
| 6,381,497 | B1 | 4/2002 | Knowlton |
| 6,381,498 | B1 | 4/2002 | Knowlton |
| 6,383,151 | B1 | 5/2002 | Diederich et al. |
| 6,387,105 | B1 | 5/2002 | Gifford, III et al. |
| 6,387,380 | B1 | 5/2002 | Knowlton |
| 6,389,311 | B1 | 5/2002 | Whayne et al. |
| 6,389,314 | B2 | 5/2002 | Feiring |
| 6,391,024 | B1 | 5/2002 | Sun et al. |
| 6,394,096 | B1 | 5/2002 | Constantz |
| 6,394,956 | B1 | 5/2002 | Chandrasekaran et al. |
| 6,398,780 | B1 | 6/2002 | Farley et al. |
| 6,398,782 | B1 | 6/2002 | Pecor et al. |
| 6,398,792 | B1 | 6/2002 | O'Connor |
| 6,401,720 | B1 | 6/2002 | Stevens et al. |
| 6,402,719 | B1 | 6/2002 | Ponzi et al. |
| 6,405,090 | B1 | 6/2002 | Knowlton |
| 6,409,723 | B1 | 6/2002 | Edwards |
| 6,413,255 | B1 | 7/2002 | Stern |
| 6,421,559 | B1 | 7/2002 | Pearlman |
| 6,423,057 | B1 | 7/2002 | He et al. |
| 6,425,867 | B1 | 7/2002 | Vaezy et al. |
| 6,425,912 | B1 | 7/2002 | Knowlton |
| 6,427,118 | B1 | 7/2002 | Suzuki |
| 6,428,534 | B1 | 8/2002 | Joye et al. |

(56) References Cited

U.S. PATENT DOCUMENTS

| | | | |
|---|---|---|---|
| 6,428,536 B2 | 8/2002 | Panescu et al. | |
| 6,430,446 B1 | 8/2002 | Knowlton | |
| 6,432,102 B2 | 8/2002 | Joye et al. | |
| 6,436,056 B1 | 8/2002 | Wang et al. | |
| 6,438,424 B1 | 8/2002 | Knowlton | |
| 6,440,125 B1 | 8/2002 | Rentrop | |
| 6,442,413 B1 | 8/2002 | Silver | |
| 6,443,965 B1 | 9/2002 | Gifford, III et al. | |
| 6,445,939 B1 | 9/2002 | Swanson et al. | |
| 6,447,505 B2 | 9/2002 | McGovern et al. | |
| 6,447,509 B1 | 9/2002 | Bonnet et al. | |
| 6,451,034 B1 | 9/2002 | Gifford, III et al. | |
| 6,451,044 B1 | 9/2002 | Naghavi et al. | |
| 6,453,202 B1 | 9/2002 | Knowlton | |
| 6,454,737 B1 | 9/2002 | Nita et al. | |
| 6,454,757 B1 | 9/2002 | Nita et al. | |
| 6,454,775 B1 | 9/2002 | Demarais et al. | |
| 6,458,098 B1 | 10/2002 | Kanesaka | |
| 6,461,378 B1 | 10/2002 | Knowlton | |
| 6,468,276 B1 | 10/2002 | McKay | |
| 6,468,297 B1 | 10/2002 | Williams et al. | |
| 6,470,216 B1 | 10/2002 | Knowlton | |
| 6,470,219 B1 | 10/2002 | Edwards et al. | |
| 6,471,696 B1 | 10/2002 | Berube et al. | |
| 6,475,213 B1 * | 11/2002 | Whayne | A61B 18/1492 600/374 |
| 6,475,215 B1 | 11/2002 | Tanrisever | |
| 6,475,238 B1 | 11/2002 | Fedida et al. | |
| 6,477,426 B1 | 11/2002 | Fenn et al. | |
| 6,480,745 B2 | 11/2002 | Nelson et al. | |
| 6,481,704 B1 | 11/2002 | Koster et al. | |
| 6,482,202 B1 | 11/2002 | Goble et al. | |
| 6,484,052 B1 | 11/2002 | Visuri et al. | |
| 6,485,489 B2 | 11/2002 | Teirstein et al. | |
| 6,488,679 B1 | 12/2002 | Swanson et al. | |
| 6,489,307 B1 | 12/2002 | Phillips et al. | |
| 6,491,705 B2 | 12/2002 | Gifford, III et al. | |
| 6,494,891 B1 | 12/2002 | Cornish et al. | |
| 6,497,711 B1 | 12/2002 | Plaia et al. | |
| 6,500,172 B1 | 12/2002 | Panescu et al. | |
| 6,500,174 B1 * | 12/2002 | Maguire | A61B 18/1492 606/41 |
| 6,508,765 B2 | 1/2003 | Suorsa et al. | |
| 6,508,804 B2 | 1/2003 | Sarge et al. | |
| 6,508,815 B1 | 1/2003 | Strul et al. | |
| 6,511,478 B1 | 1/2003 | Burnside et al. | |
| 6,511,496 B1 | 1/2003 | Huter et al. | |
| 6,511,500 B1 | 1/2003 | Rahme | |
| 6,514,236 B1 | 2/2003 | Stratienko | |
| 6,514,245 B1 | 2/2003 | Williams et al. | |
| 6,514,248 B1 | 2/2003 | Eggers et al. | |
| 6,517,534 B1 | 2/2003 | McGovern et al. | |
| 6,517,572 B2 | 2/2003 | Kugler et al. | |
| 6,522,913 B2 | 2/2003 | Swanson et al. | |
| 6,522,926 B1 | 2/2003 | Kieval et al. | |
| 6,524,299 B1 | 2/2003 | Tran et al. | |
| 6,527,765 B2 | 3/2003 | Kelman et al. | |
| 6,527,769 B2 | 3/2003 | Langberg et al. | |
| 6,529,756 B1 * | 3/2003 | Phan | A61B 18/1492 600/374 |
| 6,540,761 B2 | 4/2003 | Houser | |
| 6,542,781 B1 | 4/2003 | Koblish et al. | |
| 6,544,780 B1 | 4/2003 | Wang | |
| 6,546,272 B1 | 4/2003 | MacKinnon et al. | |
| 6,547,788 B1 * | 4/2003 | Maguire | A61B 18/00 606/41 |
| 6,549,800 B1 | 4/2003 | Atalar et al. | |
| 6,552,796 B2 | 4/2003 | Magnin et al. | |
| 6,554,780 B1 | 4/2003 | Sampson et al. | |
| 6,558,381 B2 | 5/2003 | Ingle et al. | |
| 6,558,382 B2 | 5/2003 | Jahns et al. | |
| 6,564,096 B2 | 5/2003 | Mest | |
| 6,565,582 B2 | 5/2003 | Gifford, III et al. | |
| 6,569,109 B2 | 5/2003 | Sakurai et al. | |
| 6,569,177 B1 | 5/2003 | Dillard et al. | |
| 6,570,659 B2 | 5/2003 | Schmitt | |
| 6,572,551 B1 | 6/2003 | Smith et al. | |
| 6,572,612 B2 | 6/2003 | Stewart et al. | |
| 6,577,902 B1 | 6/2003 | Laufer et al. | |
| 6,579,308 B1 | 6/2003 | Jansen et al. | |
| 6,579,311 B1 | 6/2003 | Makower | |
| 6,582,423 B1 | 6/2003 | Thapliyal et al. | |
| 6,589,238 B2 * | 7/2003 | Edwards | A61B 18/1492 606/41 |
| 6,592,526 B1 | 7/2003 | Lenker | |
| 6,592,567 B1 | 7/2003 | Levin et al. | |
| 6,595,959 B1 | 7/2003 | Stratienko | |
| 6,600,956 B2 | 7/2003 | Maschino et al. | |
| 6,602,242 B1 | 8/2003 | Fung | |
| 6,602,246 B1 | 8/2003 | Joye et al. | |
| 6,605,084 B2 | 8/2003 | Acker et al. | |
| 6,620,159 B2 * | 9/2003 | Hegde | A61B 18/1492 606/41 |
| 6,623,452 B2 | 9/2003 | Chien et al. | |
| 6,623,453 B1 | 9/2003 | Guibert et al. | |
| 6,632,193 B1 | 10/2003 | Davison et al. | |
| 6,632,196 B1 | 10/2003 | Houser | |
| 6,645,223 B2 | 11/2003 | Boyle et al. | |
| 6,648,854 B1 | 11/2003 | Patterson et al. | |
| 6,648,878 B2 | 11/2003 | Lafontaine | |
| 6,648,879 B2 | 11/2003 | Joye et al. | |
| 6,651,672 B2 | 11/2003 | Roth | |
| 6,652,513 B2 | 11/2003 | Panescu et al. | |
| 6,652,515 B1 | 11/2003 | Maguire et al. | |
| 6,656,136 B1 | 12/2003 | Weng et al. | |
| 6,658,279 B2 | 12/2003 | Swanson et al. | |
| 6,659,981 B2 | 12/2003 | Stewart et al. | |
| 6,666,858 B2 | 12/2003 | Lafontaine | |
| 6,666,863 B2 | 12/2003 | Wentzel et al. | |
| 6,669,655 B1 | 12/2003 | Acker et al. | |
| 6,669,692 B1 | 12/2003 | Nelson et al. | |
| 6,673,040 B1 | 1/2004 | Samson et al. | |
| 6,673,064 B1 | 1/2004 | Rentrop | |
| 6,673,066 B2 | 1/2004 | Werneth | |
| 6,673,090 B2 | 1/2004 | Root et al. | |
| 6,673,101 B1 | 1/2004 | Fitzgerald et al. | |
| 6,673,290 B1 | 1/2004 | Whayne et al. | |
| 6,676,678 B2 | 1/2004 | Gifford, III et al. | |
| 6,679,268 B2 | 1/2004 | Stevens et al. | |
| 6,681,773 B2 | 1/2004 | Murphy et al. | |
| 6,682,541 B1 | 1/2004 | Gifford, III et al. | |
| 6,684,098 B2 | 1/2004 | Oshio et al. | |
| 6,685,732 B2 | 2/2004 | Kramer | |
| 6,685,733 B1 | 2/2004 | Dae et al. | |
| 6,689,086 B1 | 2/2004 | Nita et al. | |
| 6,689,148 B2 | 2/2004 | Sawhney et al. | |
| 6,690,181 B1 | 2/2004 | Dowdeswell et al. | |
| 6,692,490 B1 | 2/2004 | Edwards | |
| 6,695,830 B2 | 2/2004 | Vigil et al. | |
| 6,695,857 B2 | 2/2004 | Gifford, III et al. | |
| 6,699,241 B2 | 3/2004 | Rappaport et al. | |
| 6,699,257 B2 | 3/2004 | Gifford, III et al. | |
| 6,702,748 B1 | 3/2004 | Nita et al. | |
| 6,702,811 B2 | 3/2004 | Stewart et al. | |
| 6,706,010 B1 | 3/2004 | Miki et al. | |
| 6,706,011 B1 | 3/2004 | Murphy-Chutorian et al. | |
| 6,706,037 B2 | 3/2004 | Zvuloni et al. | |
| 6,709,431 B2 | 3/2004 | Lafontaine | |
| 6,711,429 B1 | 3/2004 | Gilboa et al. | |
| 6,712,815 B2 | 3/2004 | Sampson et al. | |
| 6,714,822 B2 | 3/2004 | King et al. | |
| 6,716,184 B2 | 4/2004 | Vaezy et al. | |
| 6,720,350 B2 | 4/2004 | Kunz et al. | |
| 6,723,043 B2 | 4/2004 | Kleeman et al. | |
| 6,723,064 B2 | 4/2004 | Babaev | |
| 6,736,811 B2 | 5/2004 | Panescu et al. | |
| 6,743,184 B2 | 6/2004 | Sampson et al. | |
| 6,746,401 B2 | 6/2004 | Panescu | |
| 6,746,464 B1 | 6/2004 | Makower | |
| 6,746,474 B2 | 6/2004 | Saadat | |
| 6,748,953 B2 | 6/2004 | Sherry et al. | |
| 6,749,607 B2 | 6/2004 | Edwards et al. | |
| 6,752,805 B2 | 6/2004 | Maguire et al. | |
| 6,760,616 B2 | 7/2004 | Hoey et al. | |

(56) References Cited

U.S. PATENT DOCUMENTS

| | | | |
|---|---|---|---|
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 * | 11/2004 | Li .................... A61B 18/04 606/27 |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 * | 3/2005 | Maguire ............ A61B 18/00 604/103 |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 * | 8/2005 | LaFontaine ........ A61B 18/1485 604/916 |
| 6,923,808 B2 * | 8/2005 | Taimisto ............ A61B 18/1492 606/41 |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |

(56) References Cited

U.S. PATENT DOCUMENTS

| | | | |
|---|---|---|---|
| 7,203,537 B2 | 4/2007 | Mower | |
| 7,214,234 B2 | 5/2007 | Rapacki et al. | |
| 7,220,233 B2 | 5/2007 | Nita et al. | |
| 7,220,239 B2 | 5/2007 | Wilson et al. | |
| 7,220,257 B1 | 5/2007 | Lafontaine | |
| 7,220,270 B2 | 5/2007 | Sawhney et al. | |
| 7,232,458 B2 | 6/2007 | Saadat | |
| 7,232,459 B2 | 6/2007 | Greenberg et al. | |
| 7,238,184 B2 | 7/2007 | Megerman et al. | |
| 7,241,273 B2 | 7/2007 | Maguire et al. | |
| 7,241,295 B2 | 7/2007 | Maguire | |
| 7,241,736 B2 | 7/2007 | Hunter et al. | |
| 7,247,141 B2 | 7/2007 | Makin et al. | |
| 7,250,041 B2 | 7/2007 | Chiu et al. | |
| 7,250,440 B2 | 7/2007 | Mewshaw et al. | |
| 7,252,664 B2 | 8/2007 | Nasab et al. | |
| 7,252,679 B2 | 8/2007 | Fischell et al. | |
| 7,264,619 B2 | 9/2007 | Venturelli | |
| 7,279,600 B2 | 10/2007 | Mewshaw et al. | |
| 7,280,863 B2 | 10/2007 | Shachar | |
| 7,282,213 B2 | 10/2007 | Schroeder et al. | |
| 7,285,119 B2 | 10/2007 | Stewart et al. | |
| 7,285,120 B2 | 10/2007 | Im et al. | |
| 7,288,089 B2 | 10/2007 | Yon et al. | |
| 7,288,096 B2 | 10/2007 | Chin | |
| 7,291,146 B2 | 11/2007 | Steinke et al. | |
| 7,293,562 B2 | 11/2007 | Malecki et al. | |
| 7,294,125 B2 | 11/2007 | Phalen et al. | |
| 7,294,126 B2 | 11/2007 | Sampson et al. | |
| 7,294,127 B2 | 11/2007 | Leung et al. | |
| 7,297,131 B2 | 11/2007 | Nita | |
| 7,297,475 B2 | 11/2007 | Koiwai et al. | |
| 7,300,433 B2 | 11/2007 | Lane et al. | |
| 7,301,108 B2 | 11/2007 | Egitto et al. | |
| 7,310,150 B2 | 12/2007 | Guillermo et al. | |
| 7,313,430 B2 | 12/2007 | Urquhart et al. | |
| 7,314,483 B2 | 1/2008 | Landau et al. | |
| 7,317,077 B2 | 1/2008 | Averback et al. | |
| 7,323,006 B2 | 1/2008 | Andreas et al. | |
| 7,326,206 B2 | 2/2008 | Paul et al. | |
| 7,326,226 B2 | 2/2008 | Root et al. | |
| 7,326,235 B2 | 2/2008 | Edwards | |
| 7,326,237 B2 | 2/2008 | DePalma et al. | |
| 7,329,236 B2 | 2/2008 | Kesten et al. | |
| 7,335,180 B2 | 2/2008 | Nita et al. | |
| 7,335,192 B2 | 2/2008 | Keren et al. | |
| 7,338,467 B2 | 3/2008 | Lutter | |
| 7,341,570 B2 | 3/2008 | Keren et al. | |
| 7,343,195 B2 | 3/2008 | Strommer et al. | |
| 7,347,857 B2 | 3/2008 | Anderson et al. | |
| 7,348,003 B2 | 3/2008 | Salcedo et al. | |
| 7,352,593 B2 | 4/2008 | Zeng et al. | |
| 7,354,927 B2 | 4/2008 | Vu | |
| 7,359,732 B2 | 4/2008 | Kim et al. | |
| 7,361,341 B2 | 4/2008 | Salcedo et al. | |
| 7,364,566 B2 | 4/2008 | Elkins et al. | |
| 7,367,970 B2 | 5/2008 | Govari et al. | |
| 7,367,975 B2 | 5/2008 | Malecki et al. | |
| 7,371,231 B2 | 5/2008 | Rioux et al. | |
| 7,387,126 B2 | 6/2008 | Cox et al. | |
| 7,393,338 B2 | 7/2008 | Nita | |
| 7,396,355 B2 | 7/2008 | Goldman et al. | |
| 7,402,151 B2 | 7/2008 | Rosenman et al. | |
| 7,402,312 B2 | 7/2008 | Rosen et al. | |
| 7,404,824 B1 | 7/2008 | Webler et al. | |
| 7,406,970 B2 | 8/2008 | Zikorus et al. | |
| 7,407,502 B2 | 8/2008 | Strul et al. | |
| 7,407,506 B2 | 8/2008 | Makower | |
| 7,407,671 B2 | 8/2008 | McBride et al. | |
| 7,408,021 B2 | 8/2008 | Averback et al. | |
| 7,410,486 B2 | 8/2008 | Fuimaono et al. | |
| 7,413,556 B2 | 8/2008 | Zhang et al. | |
| 7,425,212 B1 | 9/2008 | Danek et al. | |
| 7,426,409 B2 | 9/2008 | Casscells, III et al. | |
| 7,435,248 B2 | 10/2008 | Taimisto et al. | |
| 7,447,453 B2 | 11/2008 | Kim et al. | |
| 7,449,018 B2 | 11/2008 | Kramer | |
| 7,452,538 B2 | 11/2008 | Ni et al. | |
| 7,473,890 B2 | 1/2009 | Grier et al. | |
| 7,476,384 B2 | 1/2009 | Ni et al. | |
| 7,479,157 B2 | 1/2009 | Weber et al. | |
| 7,481,803 B2 | 1/2009 | Kesten et al. | |
| 7,485,104 B2 | 2/2009 | Kieval | |
| 7,486,805 B2 | 2/2009 | Krattiger | |
| 7,487,780 B2 | 2/2009 | Hooven | |
| 7,493,154 B2 | 2/2009 | Bonner et al. | |
| 7,494,485 B2 | 2/2009 | Beck et al. | |
| 7,494,486 B2 | 2/2009 | Mische et al. | |
| 7,494,488 B2 | 2/2009 | Weber | |
| 7,494,661 B2 | 2/2009 | Sanders | |
| 7,495,439 B2 | 2/2009 | Wiggins | |
| 7,497,858 B2 | 3/2009 | Chapelon et al. | |
| 7,499,745 B2 | 3/2009 | Littrup et al. | |
| 7,500,985 B2 | 3/2009 | Saadat | |
| 7,505,812 B1 | 3/2009 | Eggers et al. | |
| 7,505,816 B2 | 3/2009 | Schmeling et al. | |
| 7,507,233 B2 | 3/2009 | Littrup et al. | |
| 7,507,235 B2 | 3/2009 | Keogh et al. | |
| 7,511,494 B2 | 3/2009 | Wedeen | |
| 7,512,445 B2 | 3/2009 | Truckai et al. | |
| 7,527,643 B2 | 5/2009 | Case et al. | |
| 7,529,589 B2 | 5/2009 | Williams et al. | |
| 7,540,852 B2 | 6/2009 | Nita et al. | |
| 7,540,870 B2 | 6/2009 | Babaev | |
| RE40,863 E | 7/2009 | Tay et al. | |
| 7,556,624 B2 | 7/2009 | Laufer et al. | |
| 7,558,625 B2 | 7/2009 | Levin et al. | |
| 7,563,247 B2 | 7/2009 | Maguire et al. | |
| 7,566,319 B2 | 7/2009 | McAuley et al. | |
| 7,569,052 B2 | 8/2009 | Phan et al. | |
| 7,582,111 B2 | 9/2009 | Krolik et al. | |
| 7,584,004 B2 | 9/2009 | Caparso et al. | |
| 7,585,835 B2 | 9/2009 | Hill et al. | |
| 7,591,996 B2 | 9/2009 | Hwang et al. | |
| 7,597,704 B2 | 10/2009 | Frazier et al. | |
| 7,598,228 B2 | 10/2009 | Hattori et al. | |
| 7,599,730 B2 | 10/2009 | Hunter et al. | |
| 7,603,166 B2 | 10/2009 | Casscells, III et al. | |
| 7,604,608 B2 | 10/2009 | Nita et al. | |
| 7,604,633 B2 | 10/2009 | Truckai et al. | |
| 7,615,015 B2 | 11/2009 | Coleman | |
| 7,615,072 B2 | 11/2009 | Rust et al. | |
| 7,617,005 B2 | 11/2009 | Demarais et al. | |
| 7,620,451 B2 | 11/2009 | Demarais et al. | |
| 7,621,902 B2 | 11/2009 | Nita et al. | |
| 7,621,929 B2 | 11/2009 | Nita et al. | |
| 7,626,015 B2 | 12/2009 | Feinstein et al. | |
| 7,626,235 B2 | 12/2009 | Kinoshita | |
| 7,632,268 B2 | 12/2009 | Edwards et al. | |
| 7,632,845 B2 | 12/2009 | Vu et al. | |
| 7,635,383 B2 | 12/2009 | Gumm | |
| 7,640,046 B2 | 12/2009 | Pastore et al. | |
| 7,641,633 B2 | 1/2010 | Laufer et al. | |
| 7,641,679 B2 | 1/2010 | Joye et al. | |
| 7,646,544 B2 | 1/2010 | Batchko et al. | |
| 7,647,115 B2 | 1/2010 | Levin et al. | |
| 7,653,438 B2 | 1/2010 | Deem et al. | |
| 7,655,006 B2 | 2/2010 | Sauvageau et al. | |
| 7,662,114 B2 | 2/2010 | Seip et al. | |
| 7,664,548 B2 | 2/2010 | Amurthur et al. | |
| 7,670,279 B2 | 3/2010 | Gertner | |
| 7,670,335 B2 | 3/2010 | Keidar | |
| 7,671,084 B2 | 3/2010 | Mewshaw et al. | |
| 7,678,104 B2 | 3/2010 | Keidar | |
| 7,678,106 B2 | 3/2010 | Lee | |
| 7,678,108 B2 | 3/2010 | Christian et al. | |
| 7,691,080 B2 | 4/2010 | Seward et al. | |
| 7,699,809 B2 | 4/2010 | Urmey | |
| 7,706,882 B2 | 4/2010 | Francischelli et al. | |
| 7,715,912 B2 | 5/2010 | Rezai et al. | |
| 7,717,853 B2 | 5/2010 | Nita | |
| 7,717,909 B2 | 5/2010 | Strul et al. | |
| 7,717,948 B2 | 5/2010 | Demarais et al. | |
| 7,722,539 B2 | 5/2010 | Carter et al. | |

(56) References Cited

U.S. PATENT DOCUMENTS

| | | |
|---|---|---|
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 * | 6/2010 | Eberl ............ A61B 18/1492 606/41 |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 * | 6/2010 | Yamazaki ........ A61B 18/1492 604/96.01 |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,277,868 B2 | 10/2012 | Kokish et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |

(56) References Cited

U.S. PATENT DOCUMENTS

| | | |
|---|---|---|
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0007071 A1* | 7/2001 | Koblish ............... A61B 18/1492 606/41 |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0087208 A1* | 7/2002 | Koblish ............... A61B 18/1492 607/113 |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0125726 A1* | 7/2003 | Maguire ............... A61B 18/00 606/41 |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0010207 A1* | 1/2005 | Swanson ............... A61B 18/1492 606/41 |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 6/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1* | 7/2005 | Maguire ............... A61B 18/00 606/41 |
| 2005/0165467 A1 | 7/2005 | Hunter et al. |
| 2005/0165488 A1 | 7/2005 | Hunter et al. |
| 2005/0171525 A1* | 8/2005 | Rioux ............... A61B 18/14 606/41 |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214312 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0021746 A1* | 1/2007 | Taimisto ............... A61B 18/1492 606/41 |
| 2007/0027390 A1 | 2/2007 | Maschke et al. |
| 2007/0043077 A1 | 2/2007 | Mewshaw et al. |
| 2007/0043409 A1 | 2/2007 | Brian et al. |

(56) References Cited

U.S. PATENT DOCUMENTS

| | | |
|---|---|---|
| 2007/0049924 A1 | 3/2007 | Rahn |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1* | 6/2007 | Matsukuma ............ A61B 18/04 606/28 |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270787 A1* | 10/2009 | Oepen ................... A61M 25/10 604/20 |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |

(56) References Cited

U.S. PATENT DOCUMENTS

| | | |
|---|---|---|
| 2010/0189876 A1* | 7/2010 | Kokish .............. A61L 29/085 427/2.3 |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1* | 2/2012 | Smith .............. A61B 18/1492 606/41 |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066315 A1* | 3/2013 | Subramaniam .... A61B 18/1492 606/41 |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1* | 7/2013 | Subramaniam ........ A61B 18/18 606/33 |

(56) References Cited

U.S. PATENT DOCUMENTS

| | | | |
|---|---|---|---|
| 2013/0172877 A1 | 7/2013 | Subramaniam et al. | |
| 2013/0172878 A1 | 7/2013 | Smith | |
| 2013/0172879 A1 | 7/2013 | Sutermeister | |
| 2013/0172880 A1 | 7/2013 | Willard | |
| 2013/0172881 A1 | 7/2013 | Hill et al. | |
| 2013/0304052 A1* | 11/2013 | Rizq | A61B 18/18 606/33 |
| 2014/0018888 A1* | 1/2014 | Ostroot | A61N 5/00 607/101 |
| 2014/0088584 A1* | 3/2014 | Royer | A61B 18/1492 606/33 |
| 2014/0088586 A1* | 3/2014 | Davis | A61B 18/1492 606/33 |
| 2014/0257280 A1* | 9/2014 | Hanson | A61B 18/1492 606/41 |
| 2014/0257281 A1* | 9/2014 | Squire | A61B 18/1492 606/41 |
| 2014/0378962 A1* | 12/2014 | Anderson | A61B 18/16 606/34 |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | 2005122938 A1 | 12/2005 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.

(56) References Cited

OTHER PUBLICATIONS

De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.

\* cited by examiner

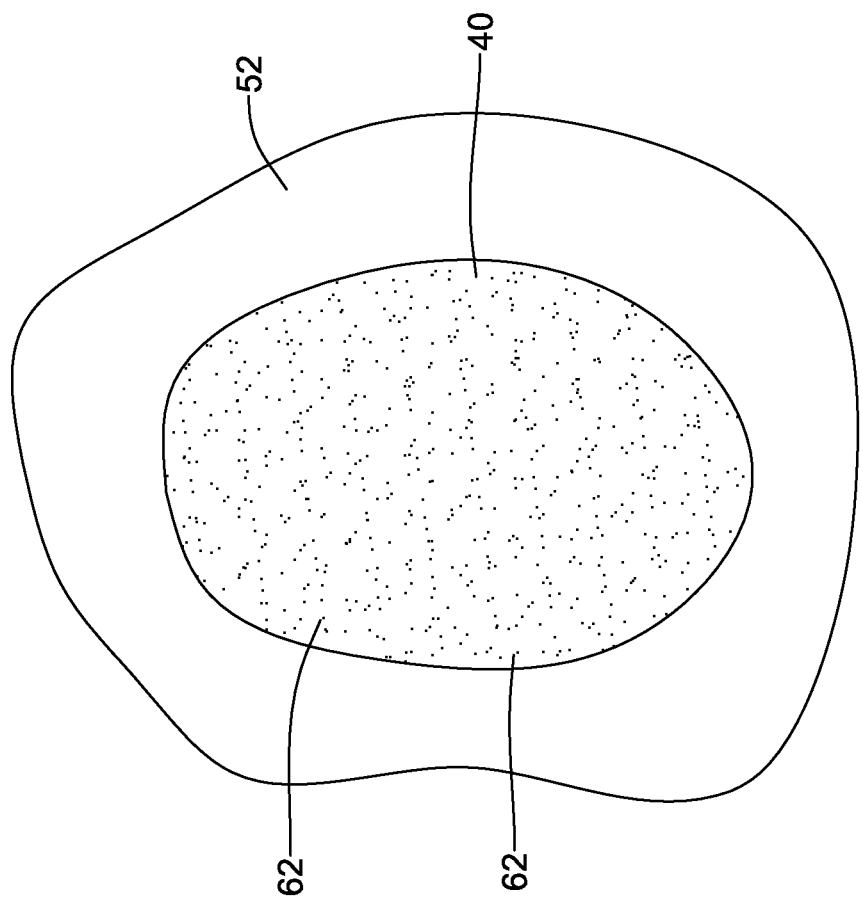

RENAL NERVE MODULATION DEVICES WITH WEEPING RF ABLATION BALLOONS

CROSS-REFERENCE TO RELATED APPLICATIONS

This application claims priority under 35 U.S.C. § 119 to U.S. Provisional Application Ser. No. 61/693,066, filed Aug. 24, 2012, the entirety of which is incorporated herein by reference.

FIELD

The invention generally pertains to percutaneous and intravascular devices for nerve modulation and/or ablation.

BACKGROUND

Certain treatments require the temporary or permanent interruption or modification of select nerve function. One example treatment is renal nerve ablation which is sometimes used to treat conditions related to congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many body tissues such as nerves, including renal nerves, brain tissue, cardiac tissue and the tissue of other body organs are in close proximity to blood vessels or other body cavities and thus can be accessed percutaneously or intravascularly through the walls of the blood vessels. In some instances, it may be desirable to ablate perivascular nerves using a radio frequency (RF) electrode. In other instances, the perivascular nerves may be ablated by other means including application of thermal, ultrasonic, laser, microwave, and other related energy sources to the vessel wall.

In treatments involving perivascular nerves such as renal nerves, treatment methods employing such energy sources have tended to apply the energy to the full circumference of the renal artery and/or vein to ensure that the nerves are modulated. However, such a treatment may result in thermal injury to the vessel wall near the electrode and other undesirable side effects such as, but not limited to, blood damage, clotting, weakened vessel wall, and/or fouling of the electrode.

SUMMARY

It is therefore desirable to provide for alternative systems and methods for tissue treatment such as intravascular nerve modulation treatments that distribute ablation or modulation sites along and around the vessel or other body cavity.

Some embodiments of the invention are directed to a balloon catheter configured for tissue modulation such as nerve modulation and/or ablation. The balloon catheter includes an inflatable balloon at or proximate a distal end of the device. The wall of the balloon is constructed so as to only allow fluid through at desired locations.

An RF transmitter extends through the lumen of the balloon to supply the RF energy. In use, the balloon is inflated with an ionically conductive fluid such as saline and positioned at a desired location for treatment. In some embodiments, the balloon may be in circumferential contact with a wall such as a blood vessel wall at the treatment location. The RF transmitter is activated and the RF energy is converted to ionic energy creating ionically charged fluid, which exits through micropores in the balloon wall to modulate or ablate tissue.

The balloon may be a multilayer balloon with a first layer made from weeping material and a second layer made from an electrically insulative material. The weeping material comprises a plurality of micro-pores and therefore has a passageway for fluid and hence ionic conduction. When a balloon is filled the micropores are therefore permeable to an ionically conductive fluid. The micropores may, or may not, permit any significant fluid flow. The weeping material may be formed by forming holes of the appropriate size in an otherwise fluid impermeable material or may be formed of a woven or knitted material to create a mesh-like structure. In other embodiments, the balloon wall may be a balloon wall having a single layer of generally non-conductive and fluid-impermeable material with the windows created by forming a pattern of micro-pores through the layer of the balloon wall.

The balloon catheter may include other elements such as a multi-lumen catheter shaft. The multi-lumen catheter shaft may include a guidewire lumen and one or two fluid lumens as well as conductive members to connect the electrode and one or more sensors to a power and control system. For embodiments that include two fluid lumens, one fluid lumen may be used to introduce the conductive fluid into the balloon and the other fluid lumen may be used to evacuate the conductive fluid from the balloon. In this manner, the conductive fluid may be circulated through the balloon. In some embodiments, it may be considered beneficial to influence the fluidic flow within the balloon by the placement of the inlet and outlet flow lumens. The RF transmitter may be constructed of any suitable material and geometry that efficiently converts RF energy to ionic energy and may, for example, be a ribbon electrode that is helically wound about the catheter shaft within the balloon lumen and may be made from any suitable material such as gold, copper, or silver.

In one illustrative method of use, a balloon catheter according to an embodiment of the invention is inserted percutaneously and/or intravascularly to a treatment location using a guidewire, a guide catheter or other conventional means. The balloon is inflated with the conductive fluid and the conductive fluid is circulated through the balloon. The transmitter is activated and RF energy is converted to ionic energy creating ionically charged fluid, which exits through micropores in the balloon wall into the tissue of the desired treatment area.

The treatment may be ended after a predetermined time or after a predetermined condition is met. For example, impedance may be measured through the electrode and the treatment may be ended after a predetermined change in the measured impedance. The above summary of some example embodiments is not intended to describe each disclosed embodiment or every implementation of the invention.

BRIEF DESCRIPTION OF DRAWINGS

The invention may be more completely understood in consideration of the following detailed description of various embodiments in connection with the accompanying drawings, in which:

FIG. 10 is a detail view of the outer surface of a balloon of another renal nerve modulation system illustrating an example window.

Figure 1:
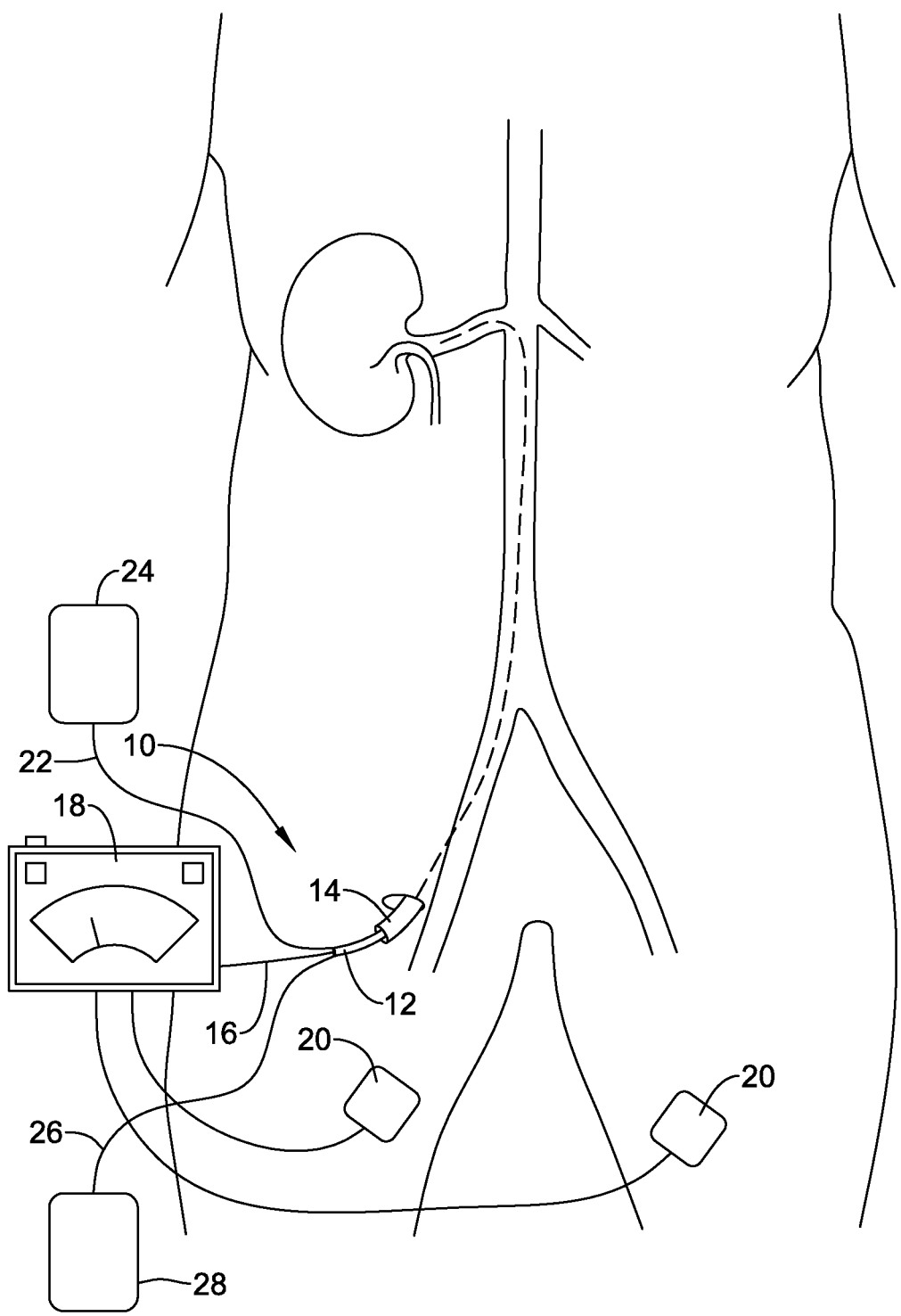
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described unless clearly stated to the contrary.

While the devices and methods described herein are discussed relative to renal nerve modulation through a blood vessel wall, it is contemplated that the devices and methods may be used in other applications where nerve modulation and/or ablation are desired. The term modulation refers to ablation and other techniques that may alter the function of affected nerves and other tissue such as brain tissue or cardiac tissue. When multiple ablations are desirable, they may be performed sequentially by a single ablation device.

FIG. 1 is a schematic view of an illustrative renal nerve modulation system 10 in situ. System 10 may include one or more conductive element(s) 16, such as wires or the like, for providing power to a renal ablation system including a renal nerve modulation device 12 disposed within a delivery sheath 14, which may be adapted to slidably contain the renal nerve modulation device 12 when the radially expanding region (not shown) of the elongate member is in a non-expanded configuration, the details of which can be better seen in subsequent figures. A proximal end of conductive element(s) 16 may be connected to a control and power element 18, which supplies necessary electrical energy to activate one or more electrodes to which the distal end of conductive element(s) 16 are attached at or near a distal end of the renal nerve modulation device 12. When suitably activated, the electrodes are capable of ablating tissue as described below. The terms electrode and electrodes may be considered to be equivalent to elements capable of ablating adjacent tissue in the disclosure which follows. Suitable materials for the delivery sheath 14, device 12 and elements capable of ablating adjacent tissue may include those materials disclosed herein (and/or other suitable materials) and may include internal and/or external layers of lubricious material(s). In some instances, return electrode patches 20 may be supplied on the legs or at another conventional location on the patient's body to complete the circuit. A proximal hub (not illustrated) having ports for a guidewire, an inflation lumen and a return lumen may also be included. A conductive fluid source 24 such as a syringe, bag, or the like may be included. The conductive fluid source 24 may include a pump, regulator valve, or the like. The conductive fluid source 24 may be fluidly connected to the device by a line 22 or other conventional means. A fluid collection device 28 such as a bag may also be fluidly connected to the device by a line 26. The fluid collection means may include an aspiration means such as a pump, syringe or the like.

The control and power element 18 may include monitoring elements to monitor parameters such as power, temperature, voltage, pulse size, impedance, and/or shape and other suitable parameters, with sensors mounted along the renal nerve modulation device 12, as well as suitable controls for performing the desired procedure. In some embodiments, the power element 18 may control a radio frequency (RF) electrode. The electrode may be configured to operate at a frequency of approximately 460 kHz. It is contemplated that any desired frequency in the RF range may be used, for example, from 450-500 kHz. It is further contemplated that other ablation devices may be used as desired, for example, but not limited to resistance heating, ultrasound, microwave, and laser devices and these devices may require that power be supplied by the power element 18 in a different form.

Figure 2:
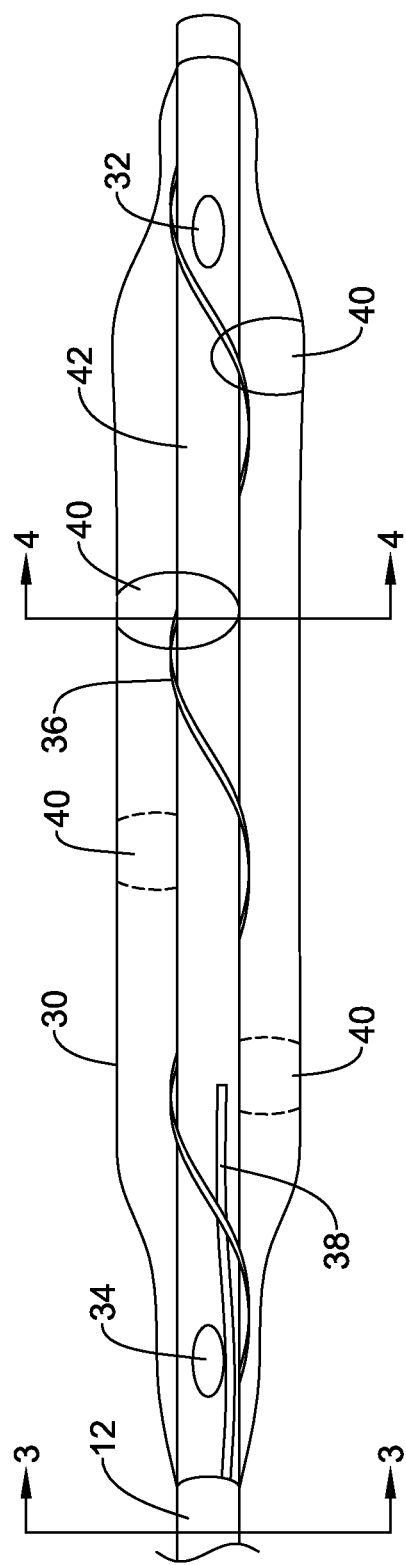
FIG. 2 is a schematic view illustrating the distal end of a renal nerve modulation system.

FIG. 2 illustrates the distal portion of a renal nerve modulation device 12. The renal nerve modulation device 12 includes a balloon 30 and an electrode 36. When in use, the balloon is preferably filled with a conductive fluid such as saline to allow the ablation energy to be transmitted from the electrode 36 through windows 40 that are permeable to RF radiation and/or energy transfer via ionic conductivity. Other appropriate conductive fluids include hypertonic solutions, contrast solution and mixtures of saline or hypertonic saline solutions with contrast solutions. The conductive fluid may be introduced through a fluid inlet port 32 and evacuated through a fluid outlet port 34, both in a central shaft 42. One or more sensors 38, such as a thermocouple, may be included and may be disposed on the shaft 42, on the balloon 30, or at another suitable location.

Figure 3:
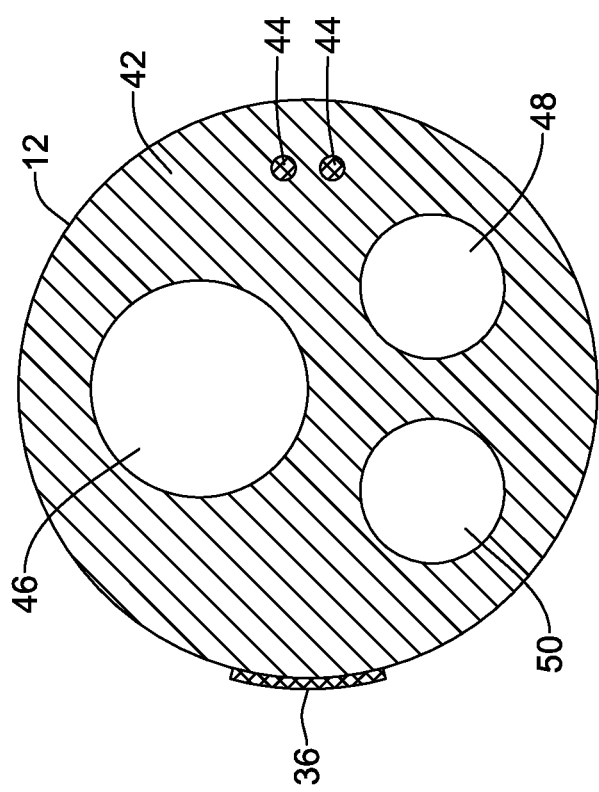
FIG. 3 is a cross-sectional view of the renal nerve modulation system of FIG. 2.

A cross-sectional view of the shaft 42 of the renal nerve modulation device 12 proximal to the balloon is illustrated in FIG. 3. The shaft 42 may include a guidewire lumen 46, a first lumen 48 (e.g., which may be connected to the fluid outlet 34), and a second lumen 50 (e.g., which may be connected to the fluid inlet 32). The electrode 36, or a conductive element to supply power to the electrode may extend along the outer surface of the shaft 42 or may be embedded within the shaft 42. The electrode 36 proximal to the balloon is preferably electrically insulated and is used to transmit power to the portion of the electrode disposed in the balloon. Conductors 44, two of which are illustrated in FIG. 3, may be used to supply power and to allow information to return from the one or more sensors 38. In some embodiments, the guidewire lumen and/or one of the fluid lumens 48, 50 may be omitted. In some embodiments, the guidewire lumen 46 extends from the distal end of the device 12 to a proximal hub. In other embodiments, the guidewire lumen 46 can have a proximal opening that is distal the proximal portion of the system 10. In some embodiments, the fluid lumens 48, 50 can be connected to a system to circulate the fluid through the balloon 30 or to a system that supplies new fluid and collects the evacuated fluid. It can be appreciated that embodiments may function with merely a single fluid lumen and a single fluid outlet into the balloon 30. It can also be appreciated that other lumen configurations are contemplated. For example, the three lumens may be disposed within each other, may be concentric, or may be non-concentric. In some embodiments, the guidewire lumen may be the innermost lumen and may be surrounded by the fluid inlet lumen, which, in turn may be surrounded by the fluid outlet lumen. In another contemplated embodiment, only one of the fluid inlet and fluid outlet lumens is disposed around the guidewire lumen and the other of the fluid inlet and fluid outlet lumens extends parallel to and spaced apart from the guidewire lumen. Another contemplated embodiment lacks the fluid outlet lumen and the fluid inlet lumen is disposed around or concentrically around the guidewire lumen. In another contemplated embodiment, the guidewire lumen is omitted and the system includes only the fluid inlet lumen or only the fluid inlet and outlet lumens. Of course, it is also contemplated that any of these shaft variations may be included with any of the balloon and window variations discussed herein. These are just examples.

Figure 4:
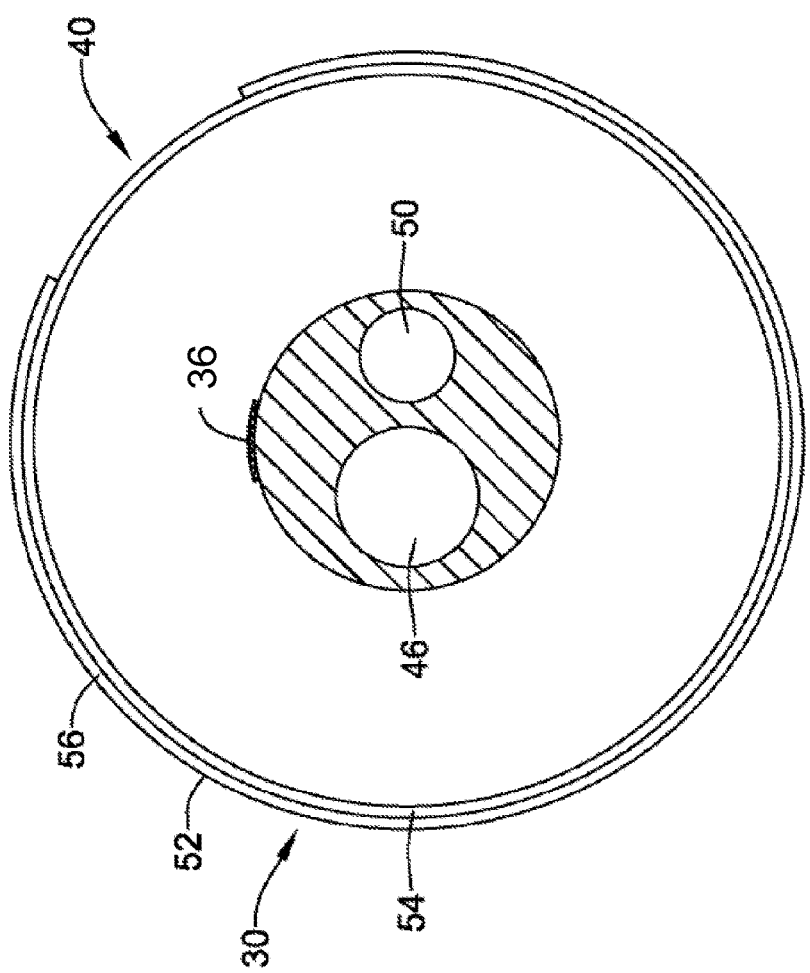
FIG. 4 is another cross-sectional view of the renal nerve modulation system of FIG. 2.

A cross-sectional view of the shaft 42 distal to the fluid outlet port 34 is illustrated in FIG. 4. The guidewire lumen 46 and the fluid inlet lumen 50 are present, as well as an electrode 36. In the presently illustrated embodiment, conductors 44, which are connected to one or more sensors 38, are not present in this cross-sectional view. It can be appreciated that in embodiments that have one or more distal sensors, one or more conductors 44 may be present to connect with then.

Balloon 30 is shown in cross-section as having a first layer 54 and a second layer 56. A window 40 is formed in the balloon 30 by the absence of the second layer 56. The first layer 54 is preferably made from a weeping material. A weeping material is a material that permits only insignificant fluid flow and does not permit the transmission of ordered streams or jets of fluid. A suitable material may be one in which micropores are formed. Micro-pores are pores having a maximum width of less than 40 micro-inches, less than 35 micro-inches, less than 30 micro-inches, or less than 25 micro-inches. Further, the micropores may have a mean pore size of between 15 and 30 micro-inches. Such a material may be formed by forming holes of a suitable size in an otherwise fluid impermeable material or by providing a material formed of a tight mesh or weave. Suitable materials include polymers materials with micropores and are produced by microporous processing of, for example, PET, nylon 12, polyamid block copolymer, polyester block copolymer, fluoropolymers such as PTFE or ePTFE, and Goretex materials; or mesh or woven materials using many polymers such as nylon or PEBA. Some embodiments may further include a reinforced substructure or a braided substructure. Suitable materials for the fibers of the substructure include UHMWPE, Kevlar, PET, carbon, and the like.

The second layer 56 may include an electrically non-conductive polymer such as a non-hydrophilic polyurethane, Pebax, nylon, polyester or block-copolymer. Other suitable materials include any of a range of electrically non-conductive polymers. In some embodiments, the materials of the first layer and the second layer may be selected to have good bonding characteristics between the two layers. In other embodiments, a suitable tie layer (not illustrated) may be provided between the two layers. As illustrated, the windows 40 are formed in the wall 52 of the balloon 30 by the absence of the second layer 56.

Figure 5:
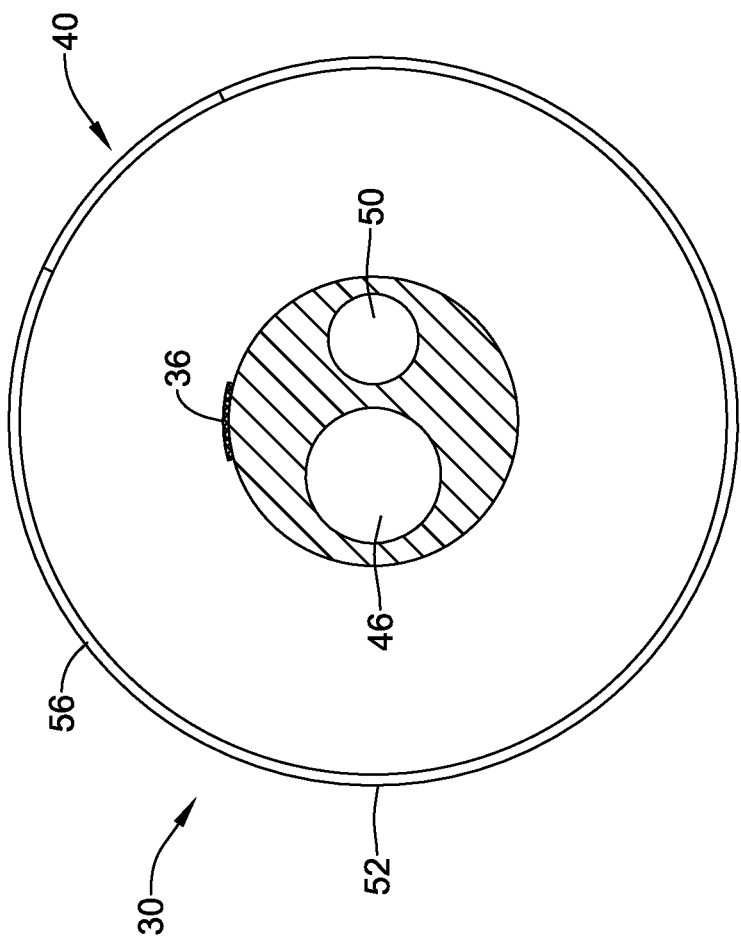
FIG. 5 is a cross-sectional view of a renal nerve modulation system.
Figure 9:
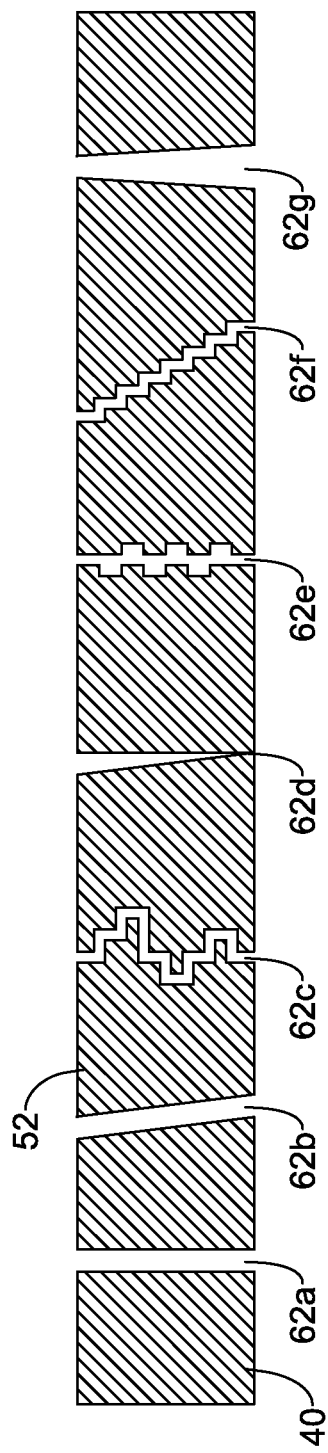
FIG. 9 is a cross-sectional view of a portion of a balloon window of a renal nerve modulation system.

FIG. 5 illustrates a cross-sectional view of another embodiment of a renal nerve modulation device. The cross-section is taken along the same lines as that of FIG. 4 and the device is similar to that of FIGS. 2-4 except as otherwise noted herein. The device of FIG. 5 has a balloon wall 52 that has a single layer 56. The layer 56 is a generally non-conductive and fluid impervious material except for the windows 40, which are formed by providing micro-pores through the balloon wall 52 at the area where the window is desired. FIG. 9 illustrates an example cross-sectional view through a portion of a window 40 through a balloon wall 52. Micropores 62a-62g illustrate some of the profiles a micropore may take. Micropores 62a-62g may be formed by a laser or through some other suitable means. FIG. 10 is a detail view illustrating an example window 40. The window 40 comprises a plurality of micropores 62. Micropores 62 may be provided in a random pattern within the boundaries of a predetermined window shape or may be provided in a regular and repeating pattern.

Figure 6:
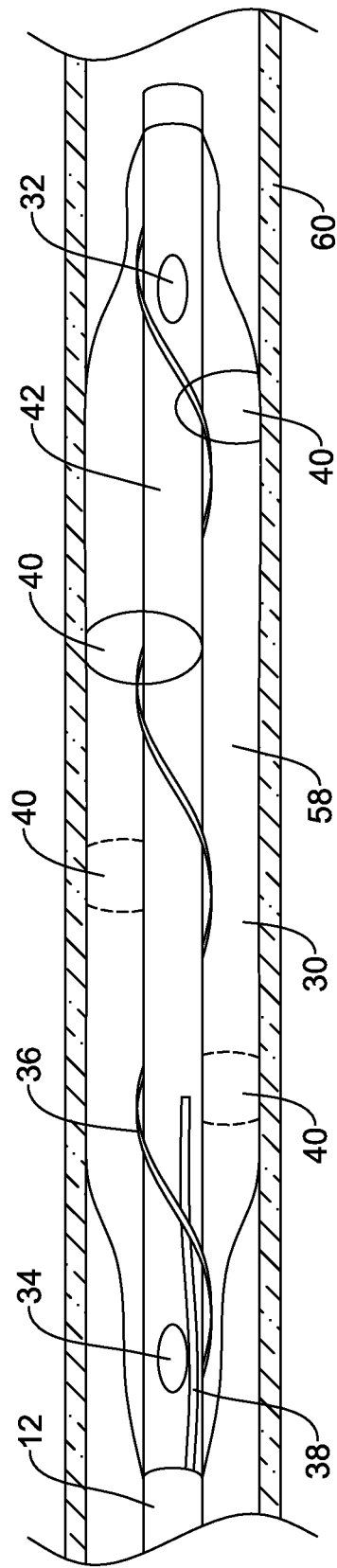
FIG. 6 is a schematic view illustrating the renal nerve modulation system of FIG. 2 in situ.

The device illustrated in FIG. 6 is similar to that of the distal end of device 12 in situ. Preferably, the device 12 is available in various sizes, and a size is selected that will allow the windows 40 of the balloon 30 to contact the wall of a blood vessel 60.

The particular balloon illustrated in FIG. 5 may be suitable for use in a renal nerve modulation application. The renal nerve extends generally longitudinally around the outside of a renal artery. This means that one can vary the longitudinal position of any particular circumferential treatment and achieve the same nerve modulation effect. Thus windows 40 are arranged to achieve complete circumferential coverage of the blood vessel while spaced apart longitudinally. In this particular case, the four windows 40 each cover a different 90 degree arc of the blood vessel. Each window may cover more than a 90 degree arc. For example, the windows 40 may cover a 100 or 110 degree arc to allow for some overlapping coverage of the windows 40. Windows 40 of this embodiment are four in number and generally circular in shape. It can be appreciated that variations in the number of windows and the shape of the windows are contemplated. For example, embodiments are contemplated which include 1, 2, 3, 4, 5, 6, 7, 8, 9, 10 or more windows and which include windows that are circular, oval, rectangular, or polygonal. Moreover, the windows having a different length and width may be oriented so that the largest dimension is parallel to the longitudinal axis, perpendicular to the longitudinal axis, or at another angle with respect to the longitudinal axis such as a 45 degree angle. In some embodiments, each window may have an aspect ratio of 2:1, 3:1 or 4:1, where the major dimension is perpendicular to the longitudinal axis of the balloon. In some embodiments, the window or windows may have a custom pattern to provide a particular treatment pattern.

The electrode 36 may be a flat ribbon electrode made from platinum, gold, stainless steel, cobalt alloys, or other non-oxidizing materials. In some instances, titanium, tantalum, or tungsten may be used. The electrode 36 may extend along substantially the whole length of the balloon 30 or may extend only as far as the distal edge of the most distal window 40. The electrode 36 may have a generally helical shape and may be wrapped around the shaft 42. In some cases, the electrode 36 may be bonded to the shaft 42. The electrode 36 and windows 40 may be arranged so that the electrode extends directly under the windows 40. In some embodiments, the electrode 36 may be a wire or may be a tubular member disposed around the shaft 42. In some embodiments, a plurality of electrodes 36 may be used and each of the plurality may be fixed to the shaft 42 under the windows 40 and may share a common connection to the conductive element 16. In other embodiments that include more than one electrode, each electrode may be separately controllable. In such embodiments, the balloon may be partitioned into more than one chamber and each chamber may include one or more electrodes. The electrode may be selected to provide a particular level of flexibility to the balloon to enhance the maneuverability of the system. It can be appreciated that there are many variations contemplated for electrode 36.

Figure 7:
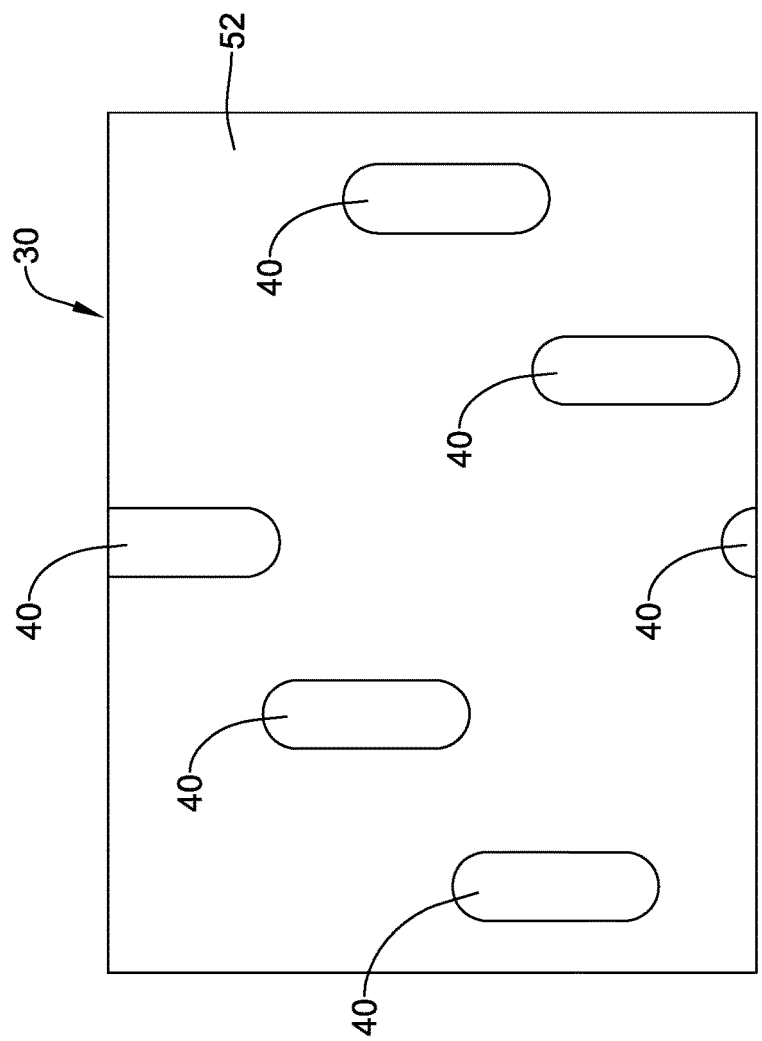
FIG. 7 is a projection view of the outer surface of a balloon of a renal nerve modulation system.
Figure 8:
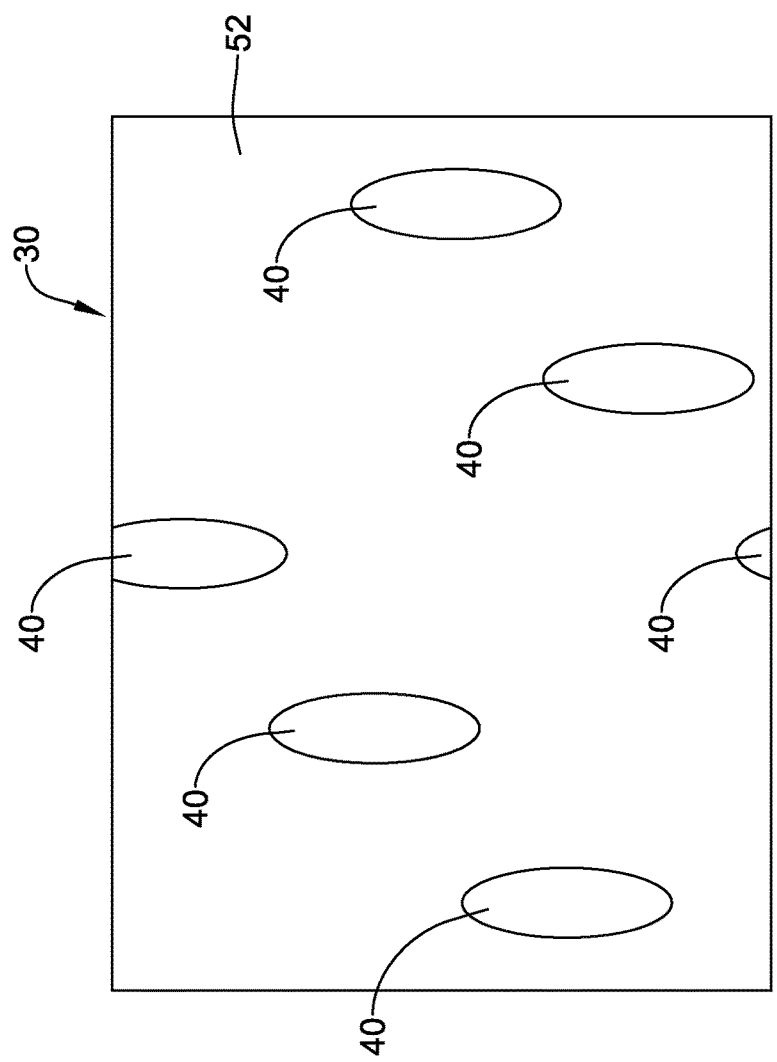
FIG. 8 is a projection view of the outer surface of a balloon of another renal nerve modulation system.

FIGS. 7-8 illustrate projections of the cylindrical central portion of a balloon wall 52 (i.e. the figure illustrates the cylindrical central portion of the balloon wall as if it were cut open and laid flat). The balloon wall 52 of these figures may be readily incorporated into any of the nerve modulation systems described herein. The balloon 30 includes a plurality of windows 40. The windows may be defined by an absence of a second layer 56 as in the FIG. 4 embodiment, or by a pattern of micropores through a single layer as in the FIG. 5 embodiment. The windows are arranged on the balloon such that their greatest dimension extends circumferentially (i.e. along a circumference of the cylindrical balloon wall) and their narrowest dimension extends axially (i.e. in the direction of the central longitudinal axis of the balloon 30). The windows 40 are arranged such that any line drawn from the proximal end of the cylindrical balloon wall to the distal end of the cylindrical balloon wall passes through at least one window.

The windows may overlap circumferentially while being spaced apart axially. If a line drawn from the proximal end of the cylindrical balloon wall to the distal end of the cylindrical balloon wall passes through two windows, those two windows are said to circumferentially overlap.

The degree of circumferential overlap may be expressed in terms of the circumferential dimension of a window 40, in terms of the circumference of the balloon or in terms of an absolute dimension. For example, two adjacent windows may exhibit circumferential overlap that is between 0.2 and 2.0 mm, that is between 0.3 and 0.7 mm, that is between 0.4 and 0.6 mm, that is at least 0.3 mm, that is at least 0.4 mm, or that is at least 0.5 mm, or that is between 20% and 30% of the circumferential dimension of one of the two windows, that is between 24% and 26% of the circumferential dimension of one of the two windows, that is between 5% and 15% of a circumferential dimension of the cylindrical balloon, that is between 6% and 7% of a circumferential dimension of the cylindrical balloon, or that is between 10% and 14% of a circumferential dimension of the cylindrical balloon, for example.

The windows 40 preferably have a greater circumferential dimension than axial dimension. For example, the ratio of circumferential dimension to axial dimension for a window may be greater than 1.5:1, greater than 2:1, greater than 7 to 1 or some other suitable number. A window may have an axial dimension of 1 mm, 1.25 mm, 1.5 mm, 1.75 mm, 2 mm, 2.25 mm, 2.5 mm or other suitable dimension and a circumferential dimension of greater than 3 mm such as 3 mm, 3.5 mm, 4 mm, 4.5 mm, 5 mm, or 7 mm. The circumferential dimension of a window 40 may be 20%, 25%, 30%, 100% or other suitable percentage of the circumferences of the cylindrical portion of the balloon wall.

The windows 40 of FIGS. 7 and 8 are shown as being arranged in a generally helical manner in that each adjacent window is offset axially and circumferentially (while overlapping circumferentially) from the previous window. Any number of windows sufficient to provide complete circumferential coverage may be used. In the embodiment of FIG. 6, five windows 40 are illustrated. Some embodiments may include 3, 4, 5, 6, 7, 8, 9, 10 or more windows and, if arranged helically as illustrated in FIG. 6, may extend for more than one turn around the balloon wall. It will be appreciated that a helical configuration is not necessary to provide complete circumferential coverage. Complete circumferential coverage means that the windows are arranged such that any axially parallel line drawn from the proximal end of the cylindrical balloon wall to the distal end of the cylindrical balloon wall passes through at least one window. The windows may be any suitable shape such as oval, oblong, bowtie or diamond shaped.

Multilayer balloons 30 having windows 40 may be made according to one of the methods described herein or by another suitable method. In one method, the first layer 54 and the second layer 56 of the balloon are manufactured separately, using blow-molding techniques or other suitable methods. Holes to define the windows 40 are formed in second layer 56 by a laser, hole punch, mechanical or hydraulic cutting element or other suitable technique. The first layer 54 is positioned inside of the second layer 56 and the two layers 54, 56 are fused together using heat, a chemical solvent, an adhesive or other suitable technique. In some cases, the two layers may be positioned inside of a mold and/or pressure may be exerted inside inner layer 54 to fuse the two layers in an expanded position using heat, solvents, or adhesives. In some instances, the two layers are not directly joined but rather are separately attached to shaft 42.

In another method of manufacture, the inner layer 54 is formed over a flexible mandrel. The flexible mandrel has a shape like that of the inner layer 54 in the expanded position but it is made from a material, such as silicon, that does not adhere well to the material of the inner layer 54. The inner layer 54 may be formed over the flexible mandrel by dip coating, spray coating, blow molding or other suitable techniques. A masking material is applied over the inner layer where the one or more windows 40 are desired. The masking material may be fixed to the inner layer using a removable or temporary adhesive. The flexible mandrel, with the inner layer and masking material thereon is then dip coated again using a non-conductive polymer to form the outer layer 56. The outer layer is cut at the edges of the masking material and the masking material along with the outer layer material that is on the masking material is removed, thus forming the balloon 30. Finally, the flexible mandrel is removed from within the balloon 30.

In use, a renal ablation system such as system 10 is provided. The system may be used with a standard guide catheter such as a 6 French guide catheter. Then the system 10 may be introduced percutaneously as is conventional in the intravascular medical device arts by using a guide catheter and/or a guide wire. For example, a guide wire such as a 0.014" diameter guidewire may be introduced percutaneously through a femoral artery and navigated to a renal artery using standard radiographic techniques. In some embodiments, a delivery sheath 14 may be introduced over the guide wire and the guide wire may be withdrawn, and the device 12 may be then introduced through the delivery sheath. In other embodiments, the device 12 may be introduced over the guidewire, or the system, including a delivery sheath 14 may be introduced over a guidewire. In embodiments involving a delivery sheath 14, the device 12 may be delivered distally from the distal end of the delivery sheath 14 into position, or the delivery sheath may be withdrawn proximally to expose the device 12. A conductive fluid 58 is introduced into the balloon through fluid inlet lumen 50 and fluid inlet port 32. The conductive fluid expands the balloon to the desired size. The balloon expansion may be monitored indirectly by monitoring the volume of conductive fluid introduced into the system or may be monitored through radiographic or other conventional means. Optionally, once the balloon is expanded to the desired size, fluid may be circulated within the balloon by continuing to introduce fluid through the fluid inlet port 32 while withdrawing fluid from the balloon through the fluid outlet port 34. The rate of circulation of the fluid may be between 0 and 100 ml/min, 2 and 45 ml/min, 3 and 30 ml/min, or other desired rate of circulation. The rate of weeping, or seepage, through the balloon windows 40 may be between 0 mL/min and 15 mL/min, between 0.1 microliter/min and 0.1 mL/min, or other desired rate (with a possible dependence on pore size and pore count). The balloon may be kept at or near a desired pressure such as an absolute pressure of between 1 and 6 atmospheres, between 1.5 and 4 atmospheres, between 2.5 and 3.5 atmospheres or other desired pressure. The electrode 36 is then activated by supplying energy to the electrode. The energy may be supplied at 400-500 kHz and at between 1 and 50 watts. The energy is transmitted through the medium of the conductive fluid and through the windows 40 to the blood vessel wall to modulate or ablate the tissue. The lack of a conductive pathway through the non-window portions of the balloon may prevent effective energy transmission through the balloon wall except at the window 40 and like structures. The progress of the treatment may be monitored by monitoring changes in impedance through the electrode. Other measurements such as pressure and/or temperature measurements may be conducted during the procedure as desired. The circulation of the conductive fluid 58 may mitigate the temperature rise of the tissue of the blood vessel 60 in contact with the windows 40. The electrode 36 is preferably activated for an effective length of time, such as 1 minute or 2 minutes. Once the procedure is finished at a particular location, the balloon 30 may be partially or wholly deflated and moved to a different location such as the other renal artery, and the procedure may be repeated at another location as desired using conventional delivery and repositioning techniques.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. An intravascular catheter, comprising:
    an elongate member having a proximal end and a distal end;
    a balloon having a longitudinal axis, an interior surface, an exterior surface, a lumen defined by the interior surface and a balloon wall extending between the interior surface and the exterior surface, the balloon having a plurality of discrete windows disposed in the balloon wall that are capable of passing an electric current between the interior surface and the exterior surface and wherein the balloon wall is otherwise electrically insulative, each of the plurality of discrete windows comprising a plurality of micropores and being spaced apart from one another by a region of the balloon wall that does not contain micropores, wherein at least two of the plurality of discrete windows only partially circumferentially overlap about the balloon with one another while being axially spaced from one another, and wherein the plurality of discrete windows are arranged in a spiral pattern that extends for a full rotation about the longitudinal axis; and
    an electrode disposed within the balloon.

2. The catheter of claim 1, wherein at least some of the plurality of micropores have an average diameter of between 15-30 micro inches.

3. The catheter of claim 1, wherein the balloon has a single balloon wall layer and wherein each of the plurality of discrete windows comprise a portion of the plurality of micropores.

4. The catheter of claim 1, wherein the balloon wall includes a first layer and a second layer,
    wherein the first layer comprises the plurality of micropores,
    wherein the second layer comprises a fluid-impermeable material, and
    wherein the plurality of discrete windows are formed by the selective omission of the second layer from portions of the balloon wall.

5. The catheter of claim 4, wherein the first layer comprises a woven material.

6. The catheter of claim 4, wherein the first layer comprises an expanded polymer material.

7. The catheter of claim 4, wherein the first layer is inside the second layer.

8. The catheter of claim 4, wherein the second layer is inside the first layer.

9. The catheter of claim 1, wherein the plurality of discrete windows are arranged such that every line extending along the balloon wall the shortest distance from the proximal end of the balloon wall to the distal end of the balloon wall passes through at least one window of the plurality of discrete windows.

10. The catheter of claim 1, wherein at least one of the plurality of discrete windows extends further in a circumferential direction than in an axial direction.

11. The catheter of claim 1, wherein at least one of the plurality of discrete windows is circular.

12. The catheter of claim 1, wherein at least one of the plurality of discrete windows is non-circular.

13. The catheter of claim 1, further comprising a temperature sensor disposed on the elongate member.

14. The catheter of claim 1, wherein the electrode is helically disposed about the elongate member.

15. A method of nerve modulation, comprising:
    inserting the intravascular catheter in accordance with claim 1 into a patient;
    moving the balloon to a region of interest;
    inflating the balloon with an electrically conductive fluid; and
    activating the electrode.

16. The catheter of claim 1, wherein the electrode is helically disposed about the elongate member.

17. The catheter of claim 1, wherein all of the plurality of discrete windows are collectively arranged in a spiral pattern that extends for a full rotation about the longitudinal axis.

18. An intravascular catheter, comprising:
    an elongate member having a proximal end and a distal end;
    a balloon having a longitudinal axis, an interior surface, an exterior surface, a lumen defined by the interior surface and a balloon wall extending between the interior surface and the exterior surface, the balloon having a plurality of discrete weeping windows disposed in the balloon wall and able to pass an electric current between the interior surface and the exterior surface and wherein the balloon wall is otherwise electrically insulative, the plurality of discrete weeping windows being spaced apart from one another by a non-weeping region of the balloon wall wherein the plurality of discrete weeping windows only partially circumferentially overlap about the balloon with each other and are spaced axially from each other, and wherein the plurality of discrete weeping windows are arranged in a spiral pattern that extends for a full rotation about the longitudinal axis, and wherein the plurality of discrete weeping windows are arranged such that every line extending along the balloon wall the shortest distance from the proximal end of the balloon wall to the distal end of the balloon wall passes through at least one discrete weeping window; and
    an electrode disposed in the balloon.

19. The catheter of claim 18, wherein each of the plurality of discrete weeping windows comprises a plurality of micropores.

20. The catheter of claim 18, wherein all of the plurality of weeping discrete weeping windows are collectively arranged in a spiral pattern that extends for a full rotation about the longitudinal axis.

* * * * *